(12) United States Patent
Ballerstadt et al.

(10) Patent No.: US 6,454,710 B1
(45) Date of Patent: Sep. 24, 2002

(54) DEVICES AND METHODS FOR MONITORING AN ANALYTE

(75) Inventors: Ralph Ballerstadt, Palatine, IL (US); Anthony Polak, Lake Zurich, IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/832,575

(22) Filed: Apr. 11, 2001

(51) Int. Cl.[7] .................................................. A61B 5/00
(52) U.S. Cl. .................. 600/365; 600/316; 600/317; 600/322; 204/403.06; 204/415
(58) Field of Search .................. 600/316, 317, 600/322, 365; 204/403, 414, 415; 356/39

(56) References Cited

U.S. PATENT DOCUMENTS

| | | |
|---|---|---|
| 3,877,784 A | 4/1975 | Lin |
| 4,058,732 A | 11/1977 | Wieder |
| 4,150,295 A | 4/1979 | Wieder |
| 4,344,438 A | 8/1982 | Schultz |
| 4,737,464 A | 4/1988 | McConnell et al. |
| 4,791,310 A | 12/1988 | Honig et al. |
| 5,061,076 A | 10/1991 | Hurley |
| 5,143,066 A * | 9/1992 | Komives et al. ............ 600/317 |
| 5,156,972 A * | 10/1992 | Issachar ..................... 422/68.1 |
| 5,496,997 A | 3/1996 | Pope |
| 5,660,848 A | 8/1997 | Moo-Young |
| 5,756,115 A | 5/1998 | Moo-Young |
| 5,814,449 A | 9/1998 | Schultz et al. |
| 5,871,628 A | 2/1999 | Dabiri et al. |
| 5,990,479 A | 11/1999 | Weiss |
| 5,995,860 A | 11/1999 | Sun et al. |
| 6,002,954 A | 12/1999 | Van Antwerp et al. |
| 6,011,984 A | 1/2000 | Van Antwerp et al. |
| 6,110,630 A | 8/2000 | Reddy et al. |
| 6,114,350 A | 9/2000 | Randall et al. |
| 6,163,714 A | 12/2000 | Stanley et al. |
| 6,177,684 B1 | 1/2001 | Sugiyama |
| 6,256,522 B1 * | 7/2001 | Schultz ..................... 600/317 |

FOREIGN PATENT DOCUMENTS

| | | |
|---|---|---|
| EP | 0761159 A3 B1 | 3/1998 |
| WO | WO 00/20862 | 4/2000 |

OTHER PUBLICATIONS

Sohrab Mansouri and Jerome S. Schultz "A Miniature Optical Glucose Sensor On Affinity Binding", Biotechnology, 1984, pp. 885–890.

W. Rudolf Seitz, "Optical Sensors Based In Immobilized Reagents", Biosensors Fundamentals and Applications, Oxford University Press, copyright 1987, pp. 599–603.

D. L. Meadows and J. S. Schultz, "Design, Manufacture and Characterization of an Optical Fiber Glucose Affinity Sensor Based on An Homogeneous Fluorescence Energy Transfer Assay System", Analytica Chimica Acta 280, 1993, pp. 21–30.

Klaus Mosbach and Olof Ramström, "The Emerging Technique of Molecular Imprinting and Its Future on Biotechnology", Bio/Technology vol. 14, 1996, pp. 163–170.

(List continued on next page.)

*Primary Examiner*—Kevin Shaver
*Assistant Examiner*—Patricia Mallari

(57) ABSTRACT

A device for monitoring an analyte is described, which includes (a) a support having an interior surface and an exterior surface; (b) a substrate connected to the interior surface of the support; (c) a spacer connected to the interior surface of the support and encompassing the substrate; and (d) a first membrane, permeable to the analyte, having an interior surface and an exterior surface, the interior surface being connected to the spacer. A chamber that encloses the substrate is defined by the interior surface of the support, the spacer, and the interior surface of the first membrane. The spacer exceeds the substrate in elevation such that a void volume exists between the interior surface of the first membrane and the substrate. A method of using the device for the transdermal monitoring of an analyte is also described.

42 Claims, 2 Drawing Sheets

OTHER PUBLICATIONS

Margaret A. Hines et al., Synthesis and Characterization of Strongly Liminescing ZnS–Capped CdSe Nanocrystals, J. Phys. Chem., 100, 1996, pp. 468–471.

Dmitri Ivnitski et al., "Biosensors for Detection of Pathogenic Bacteria", Biosensors and Bioelectronics 14, 1999, pp. 599–624.

Ryan J. Russell et al., "A Flourecense–Based Glucose Biosensor Using Concanavalin A and Dextran Encapsulated In A Poly(ethylene glycol) Hydrogel", Analytical Chemistry Vo. 71, No. 15, 1999, pp. 3126–3132.

M. Dittrich et al., "Branched Oligoester Microspheres Fabricated By A Rapid Emulsion Solvent Extraction Method", J. Microencapsulation, vol. 17, No. 5, 2000, pp. 587–598.

J. Molpeceres et al., "Biodegradable Nanoparticles As A Delivery System For Cyclosporine: Preparation and Characterization", J. Microencapsulation, vol. 17, No. 5, 2000, pp. 599–614.

Ralph Ballerstadt and Jerome S. Schultz, "A Fluorescence Affinity Hollow Fiber Sensor For Continuous Transdermal Glucose Monitoring", Analytical Chemistry vol. 72, No. 17, 2000, pp. 4185–4192.

The Nut Factory: Kitchen: Interesting Facts: Chocolate Panning:, "Panning Nuts in Chocolate", <http://www.thenutfactory.com/kitchen/facts–chocolate–panning.html>, Mar. 16, 2001, pp. 1–4.

John Franjione, Ph. D. et al.—Technology Today—Art & Science Microencapsulation, "The Art and Science of Microencapsulation", <http://www.swri.org/3pubs/ttoday/summer/microeng.htm>, Mar. 16, 2002, pp. 1–7.

* cited by examiner

DEVICES AND METHODS FOR MONITORING AN ANALYTE

BACKGROUND

The present invention relates to devices and methods for monitoring an analyte and, more particularly, to devices and methods for transdermal monitoring of an analyte.

The monitoring of certain analyte concentrations in the body enables early detection of health risks, and identifies the need for the introduction of therapeutic measures. One of the most commonly monitored analytes is glucose. The concentration of glucose in the blood is an important parameter which determines the appropriate dosages of insulin for diabetics. Various methods have been developed for monitoring glucose levels in the blood, including methods conducted in vivo. For example, an implantable fluorescence affinity hollow fiber sensor has been reported for the continuous transdermal monitoring of glucose in the blood (see, for example, *Analytical Chemistry* Vol. 72, No. 17, pp. 4185–4192). The interiors of such hollow fiber sensors are packed with cross-linked dextran beads and fluorescently-tagged bioreagents that display fluorescence changes with rising concentrations of glucose. Detection of the fluorescence is achieved extracorporeally (e.g., with an optical unit incorporating a laser and a photodetector) and is correlated with a concentration of glucose in the blood.

Unfortunately, the use of hollow fiber sensors for monitoring glucose in the blood suffers from a number of drawbacks. First, due to the narrow width of the fibers (ca. 200 microns) and the unpredictable ratio of dextran bead volume to void volume, reproducible packing of the interiors is extremely difficult, and leads to irreproducibility of fluorescence readings between fibers. Second, the narrow cross-section of the fibers results in weak fluorescence signals which are difficult to detect. Third, the fibers are delicate and prone to kinks, which complicates both the implantation and explantation of the fibers in the subcutaneous tissue. Fourth, the mobility of the cross-linked dextran beads in the fiber can result in the interposition of a bead between the excitation light from the laser and a fluorescently-tagged bioreagent, thus resulting in reduced signal.

The present invention is directed to overcoming these and other disadvantages inherent in hollow fiber sensors.

SUMMARY

The scope of the present invention is defined solely by the appended claims, and is not affected to any degree by the statements within this summary.

Briefly stated, a device for monitoring an analyte embodying features of the present invention includes (a) a support having an interior surface and an exterior surface; (b) a substrate connected to the interior surface of the support, wherein the substrate is opaque; (c) a spacer connected to the interior surface of the support; (d) a labeled analogue, which binds reversibly to the substrate; and (e) a first membrane having an interior surface and an exterior surface, wherein the interior surface is connected to the spacer. The first membrane is permeable to the analyte and impermeable to the labeled analogue, and the first membrane is substantially transparent to each of an excitation wavelength and an emission wavelength of the fluorescent label. The dye absorbs a majority of the excitation and emission wavelengths of the fluorescent label. A chamber which encloses the substrate and the labeled analogue is defined by the interior surface of the support, the spacer, and the interior surface of the first membrane. The spacer exceeds the substrate in elevation such that a void volume exists between the interior surface of the first membrane and the substrate.

A method for monitoring an analyte embodying features of the present invention includes (a) implanting into a subcutaneous region of a patient a device in accordance with the present invention; (b) illuminating an extracutaneous region of the patient with a light having a wavelength which corresponds to the excitation wavelength of a fluorescently-labeled analogue contained in the device; (c) detecting a fluorescence signal corresponding to the emission wavelength of the fluorescently-labeled analogue using an extracutaneous photodetector; and (d) correlating the fluorescence signal with a concentration of the analyte.

The presently preferred embodiments described herein may possess one or more advantages relative to hollow fiber sensors, which can include but are but not limited to: higher fluorescence yields; reproducible introduction of bioreagents during manufacture of device; preservation of physical integrity of device during implantation and explantation; improved reproducible positioning of extracorporeal photodetector; significantly improved signal-to-noise ratio; and minimization of undesirable random fluorophore shadowing effects.

DETAILED DESCRIPTION OF THE INVENTION

Figure 1:
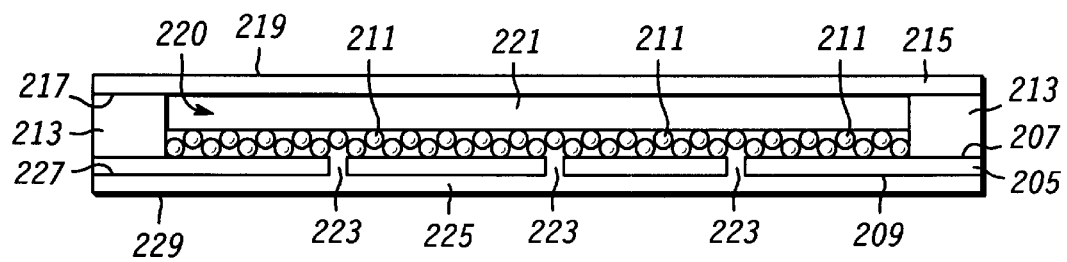
FIG. 1 is a cross-sectional side view of a device embodying features of the present invention.

The devices and methods for monitoring an analyte in accord with the present invention are based on a competitive reaction for the binding site of the substrate between the analyte of interest and a fluorescently-labeled analogue. At low concentrations of analyte, the fluorescently-labeled analogue binds to the substrate. As the concentration of analyte increases, the fluorescently-labeled analogue dissociates from the substrate. The substrate absorbs a majority of the excitation and emission wavelengths of the fluorescent label (e.g., by the action of a dye attached to the substrate), such that in the presence of light corresponding to the excitation wavelength, minimum fluorescence is generated when the labeled analogue resides within the substrate (i.e., when the concentration of analyte is low). Contrariwise, increased fluorescence is detected when the labeled analogue resides outside the substrate (i.e., when the concentration of analyte is high). By measuring the fluorescence over a range of analyte concentrations, a correlation can be established between the magnitude of a fluorescence signal and the concentration of analyte giving rise to the signal.

Definitions

"Shadowing" refers to (1) the absorption of incoming light by a substrate, and (2) the undesirable interposition of an object (e.g., substrate) between light and a fluorescently-labeled material.

"Void volume" describes a region having a low density of substrate, in which fluorescence is generated.

Analyte

"Analyte" refers to one or a plurality of species having a concentration of interest.

The nature of the analyte monitored in accord with the present invention is unrestricted, provided the labeled analogue and the substrate are appropriately matched therewith to ensure competitive binding reaction between the labeled analogue and the analyte. Preferred analytes include but are not limited to glucose, coumadin, synthroid, cyclosporin, erythropoietin, lopid, monopril, digoxin, amiodarone, prothrombin, cytokines, chemokines, creatinine, lactate, and various chemotherapeutic drugs, such as taxol and fluorouracil. The present invention can be adapted for simultaneous monitoring of multiple analytes by including substrates and labeled analogues matched to each of the analytes of interest.

Labeled Analogue

"Analogue" refers to one or a plurality of ligands that binds to the substrate at low analyte concentrations, and dissociates from the substrate as the concentration of analyte increases. "Labeled analogue" and the like refer to an analogue that is fluorescently-labeled.

In the absence of analyte, labeled analogues mostly reside within the pores of the porous support. The labeled analogues affinity bind to the binding substrate, but can also affinity bind to the analyte. When analyte diffuses through the membrane into the device, the analyte binds to the labeled analogue, and displaces the labeled analogues from the binding substrate. Following displacement, the labeled analogues migrate to the void-volume, at which point their emission wavelength can be detected upon excitation. As the concentration of analyte increases, a greater percentage of the labeled analogues reside in the void-volume, thereby increasing the intensity of label emission.

In certain embodiments, the labeled analogue binds only to the substrate by affinity binding. When analyte diffuses through the membrane into the device, the analyte displaces the labeled analogue from the binding substrate. Following displacement, the labeled analogues migrate to the void-volume, at which point their emission wavelength can be detected upon excitation. As the concentration of analyte increases, a greater percentage of the labeled analogues reside in the void-volume, thereby increasing the intensity of label emission. The labeled analogue can be any molecule that is too large to pass through the analyte-permeable membrane, but small enough to enter the porous-support and affinity bind to the analyte or substrate.

Attached to the analogue by a covalent bond or other means is a fluorescent label. When irradiated with an appropriate excitation wavelength, the label emits light at a first wavelength which may be detected outside of the body. Although the excitation wavelength is preferably generated by a visible or infrared laser, any suitable electromagnetic radiation from X-ray to infrared may be used. Light and electromagnetic radiation from X-ray to infrared are synonymous as used herein.

The fluorescent label can be any label that fluoresces when irradiated. A broad variety of fluorescent labels are known in the art and are commercially available, for example, from Molecular Probes, and Pharmacia.

Suitable fluorescent labels include the succinimidyl ester dyes sold under the tradename ALEXA FLUOR (Molecular Probes, Inc., Eugene, Oreg., USA), and the cyanine dyes sold under the tradenames CY5 and CY5.5 (Amersham Pharmacia, Piscataway, N.J.). The CY5 and CY5.5 cyanine dyes are prepared with succinimidyl ester reactive groups. The number immediately after "Cy" indicates the number of bridge carbon atoms, while the number following the decimal point indicates a unique dye structure determined by the particular substituents.

Especially preferred dyes include the ALEXA FLUOR dyes, especially ALEXA633, which has an excitation wavelength of 633 nm, and an emission wavelength of 647 nm.

Support

Suitable supports in accordance with the present invention include silicones, fluorosiloxanes, epoxies, acrylate derivatives (e.g. methyl methacrylate), polyamides, polyimides ceramics (e.g. silica, porous silica), and halogenated hydrocarbons (e.g. PVC, PTFE).

Substrate

"Substrate" refers to one or a plurality of immobilized receptors having at least one binding site and, more preferably, having a plurality of binding sites.

In preferred embodiments, the substrate is opaque (i.e., substantially impenetrable by light), and has a large surface area containing multiple binding sites. Preferably, the substrate comprises a plurality of pores having a porosity sufficiently large to permit ingress and egress of the flourescently-labeled analogue. The substrate may be intrinsically opaque (e.g., a porous alumina), or modified in such a way so as to absorb a majority of the excitation and emission wavelengths of the fluorescent label (e.g., by the action of a dye attached to the substrate).

Suitable porous materials include but are not linuted to cross-linked dextran beads (such as SEPHADEX), agarose, SEPHAROSE®, ceramic, alumina, charcoal, and silica.

Preferably, the substrate is cross-linked dextran beads having a plurality of binding sites within the pores.

For embodiments utilizing glucose binding sites, such sites are already provided by the glucose termini of the cross-linked dextran bead. For embodiments utilizing binding sites other than glucose (e.g., Concanavalin-A), the desired sites can be introduced into the beads by the modification procedures described hereinbelow.

Preferably, the substrate has a diameter ranging from about 10 microns to about 500 microns, and more preferably from about 10 microns to about 50 microns. More preferably, the substrate has a diameter of about 25 microns.

Immobilization of the substrate on the support can be achieved by physical means (e.g., by an adhesive) or by chemical means (e.g., by covalent bonding). For embodiments in which the substrate corresponds to a plurality of dextran beads, the beads can conveniently be physically immobilized to the support with a pressure sensitive adhesive (PSA) or a hydrogel.

The PSA or hydrogel can be applied directly to second membrane 225, and substrate 211 attached directly thereto.

A preferred adhesive for use in accord with the invention is a double-coated acrylic foam tape and adhesive transfer tape sold under the tradename of VHB (3M, Minneapolis, Minn.).

The substrate preferably coats about 50% to 90% of the support. More preferably, coverage of the support is as complete as possible.

The thickness of the layer of support coated onto the support is preferably less than about 200 microns. More preferably, the thickness is less than about 100 microns.

Dye

Suitable dyes in accordance with the present invention have a broad absorption spectrum that overlaps the fluorescence excitation and emission spectra of the fluorescent label, thereby minimizing fluorescence from the fluorescent label. In such instances, the dyed substrate provides a "light-blocking layer" which minimizes or prevents fluorescence from the fluorescently-labeled analogue when the concentration of analyte is low.

Preferred dyes include but are not limited to Alkali Blue 6B, Azure A, Evans Blue (Direct blue 53), and Celestine blue. Preferably, the dye is Alkali Blue 6B, which has a broad absorption spectrum from 500 nanometers to 700 nanometers. Other useful quenching-dyes include Safranin and Pararosaniline.

The dye is linked to the substrate, either physically or chemically. Preferably, the dye is covalently linked to the bead. Preferably, the dye is attached to the substrate by means of a bifunctional linker. More preferably, the dye is attached using the DVS (i.e., divinyl sulfone) method, as described in *Analytical Chemistry* Vol. 72, No. 17, p. 4186.

Preferably, the substrate contains about 0.5 to about 5.0 micromole of dye per mL of a wet suspension of substrate. More preferably, the substrate contains about 1.0 to about 3.0 micromole/mL. Still more preferably, the substrate contains about 2.0 to about 3.0 micromole/mL.

In embodiments in which the analyte of interest is glucose, and the fluorescently-labeled analogue is Concanavalin-A labeled with ALEXA633, a preferred dye for the substrate is Alkali Blue 6B.

Spacer

For in vivo applications, it is preferred that the spacer is a biocompatible material. Preferred materials include, but are not limited to, titanium, stainless steel, PTFE, silica, silicon nitride, silicones, fluorosiloxanes, or minimally biocompatible (or non biocompatible) materials treated with substances that enhance biocompatibility, such as PEG (polyethylene glycol), or angiogenic materials (such as basic fibroblast growth factor-bFGF).

The height of the spacer governs the size of the void volume, which in turn affects the diffusion time of fluorescently labeled analogues from the "light blocking" environment of substrate into the transparent environment of the void volume. This effect on the diffusion time in turn affects the response time of the device.

Figure 3:
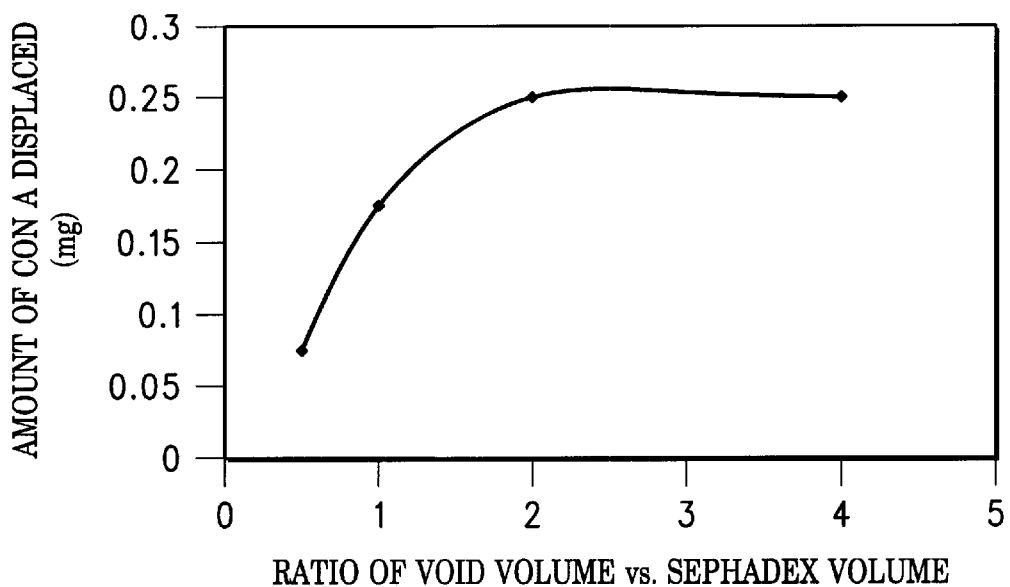
FIG. 3 is a plot of the amount of Con-A displaced vs. the void volume to SEPHADEX ratio.

The height of the void volume between substrate and membrane is preferably between about 50 and about 500 microns. More preferably, the height is between about 75 and about 400 microns. Still more preferably, the height is between about 100 and about 300 microns. The ratio of void volume to the volume occupied by the substrate determines the intensity of the fluorescent light that is emitted from the implanted device. For example, a fixed volume of a suspension of SEPHADEX loaded with Concanavalin A was pipetted into 1.5 ml tubes. Various volumes of phosphate buffered solution (pH 7.2) with or without 20 mM glucose were added. The concentration of displaced Concanavalin A (Con A) in the supernatant was then measured. The results are plotted in FIG. 3, which shows the relationship between the amount of Con A displaced (which is proportional to fluorescent signal intensity) and the ratio of void volume to volume occupied by SEPHADEX.

The ratio of void volume to the volume occupied by substrate is preferably between about 1:1 to 5:1. More preferably, this ratio is less than about 3:1. Still more preferably, this ratio is about 1:1.

The spacer can be attached to the support by physical means with an adhesive (e.g., methyl methacrylate, acrylate derivatives), or by chemical means (e.g., by using an epoxy or cyanoacrylate ester).

Membrane

The analyte-permeable membrane encloses the components of the device and allows the analyte to enter and exit the device while trapping the device components. That is, the membrane of the present invention can be made of any material impermeable to the labeled analogue but permeably to the analyte. The membrane is preferably comprised of a biocompatible material. When more than one membrane is present, the materials can be the same or different.

Suitable materials include, but are not limited to, cellulose acetate, silicones, fluorosiloxanes, polysulfones, polycarbonates, poly(vinyl chlorides), polyamides, ethylene vinyl acetate copolymers, poly(vinylidene) fluoride, poly (urethanes), poly(benzimidazoles), cellulose esters, cellulose triacetate, cellulose, cellulose nitrate, regenerated cellulose, cross-linked poly(vinylpyrrolidone); crosslinked polyacrylamide, and crosslinked poly (hydroxy ethyl methacrylate). More preferably, membranes in accord with the present invention are cellulose acetate.

The thickness of the membrane is preferably between about 10 to 200 microns. More preferably, the thickness is between about 15 to 100 microns. Still more preferably, the thickness is about 20 microns.

For embodiments in which the analyte of interest is glucose, cellulose acetate is preferred. When the labeled analogue is Con A, the membrane typically has a molecular weight cutoff of about 10 kDa. When the labeled analogue is Dextran, the membrane typically has a molecular weight cutoff of about 10 kDa.

The analyte permeable membrane can be attached to the spacer by physical means by use of an adhesive (e.g., methyl methacrylate, or acrylic derivatives), or by chemical means (e.g. by using an epoxy, cyanoacrylate, or cyanoacrylate ester.

Reference

A well-known problem associated with fluorescent dyes and optical measurements is that the fluorescent response (intensity) of an optical sensor is dependent on the intensity of the light that irradiates it. The intensity of the light that strikes the optical sensor is in turn dependent upon the optical path length, the absorptivity and scattering of the media that the light must travel through before reaching the monitoring device, and the path the fluorescent signal must take in order to reach the detector. In addition, any variation in the intensity of the power output of the light emitting device will be interpreted as a change in the concentration of the analyte.

Various approaches have been used to solve this problem. One strategy is to incorporate a separate internal reference dye in the sensor.

The reference dye can be an organic dye, which fluoresces at a substantially different wavelength than the dye attached to the analogue. The excitation wavelength of the reference dye can be the same as the dye attached to the analogue or different.

By physically moving the light source and photodetector, the intensity of the reference dye can be monitored and optimized. Since the reference dye is part of the implanted package, light from the reference and labeled analogue dye travel substantially the same path to the detector, resulting in a similar attenuation due to scattering, absorption and path length. Therefore, by ratioing the intensity of the labeled analogue to reference intensity, any effects due to scattering, absorptivity (e.g., skin color) or path length is removed.

Examples of suitable reference dyes for use in accord with the present invention include but are not limited to: tracer dyes composed of two proprietary dyes in a polystyrene sphere which can be purchased from Molecular Probes (Eugene, Oreg.), and phycobiliproteins (PBXL3, Martek Bioscience Corp. Columbia, Md.).

Alternatively, the reference can be a quantum dot. Quantum dots are particles that measure only a few nanometers in diameter. They come in a nearly unlimited palette of colors and can be linked to other molecules (e.g., bio-molecules including proteins and polynucleotides, glass, and plastic) to adjust their solubility. The emission wavelength of quantum dots can be varied by varying the size of the nanoparticles, and can be used to make a rainbow of colors with white light or a single-color laser. Furthermore, the quantum dots have better photostability than traditional organic reference dyes. If used, the quantum dot particle can be physically or chemically attached to the substrate, to a glass bead that is separately attached to the support, or to the support itself.

The reference can be placed anywhere in the device, including within or on the analyte permeable membrane, the support, the substrate, or the void volume. It is preferably placed in the void volume.

Further, it is preferred that the analyte permeable membrane be impermeable to the reference such that the concentration of reference in the device remains constant. Fluorescence of the reference is not affected by the presence or absence of analyte. Thus, the ratio of signal from the reference to the signal that depends on concentration of analyte should remain constant regardless of the location of the photodetector.

It is preferred that excitation of the reference and the labeled analogue be achieved at the same wavelength, but that the reference dye emit at a different and, preferably, longer wavelength. A substantial red shift in the emission of the reference ensures no or minimum overlap between the fluorescence signal from the labeled analogue, and the fluorescence signal from the reference. By incorporation of the appropriate band-pass filter in front of the photodetector of the optical unit (to detect light from the labeled analogue), light longer than a certain wavelength, such as the fluorescent emission from the reference, will be prevented from reaching the detector.

One benefit of placing a reference in close proximity to the fluorescent label is the ability to maximize the emission intensity available from both the fluorescent label and the reference. When the analyte sensing device is implanted in a human, and the excitation source or laser is above the skin, the invariant (analyte independent) nature of the reference emission may be used to focus the excitation beam on the device. Greater precision in focusing the excitation beam, allows for a lower analyte emission requirement; therefore, a smaller device is possible. Accurate focusing allows for a smaller implant.

The molar ratio of reference fluorochromes to analogue fluorochromes is preferably be about 0.01 to about 1.0.

Device

Preferably, devices in accord with the present invention are substantially flat. Flat geometries provide large cross-sectional areas, which enable increased detection of fluorescent signals emanating from the void volume, and relax the degree of precision required in placing an extracutaneous light source and photodetector exactly in line with the implanted device. Hence, reproducibility of fluorescence measurements is increased. For example, the extracutaneous positioning of a light source and photodetector having a spot size of 1 mm can vary by about +/−4.5 mm and still provide an accurate result when used with an implanted device having a cross-sectional area of 10×10 mm². Considerably less variation would be tolerated in the contrasting case of an implanted hollow fiber sensor, which has a diameter on the order of about 200 microns.

In addition, devices in accord with the present invention are preferably thin, as controlled by the height of the spacer, in order to minimize the response time of the sensor. Thinner devices correspond to shorter diffusion times for fluorescently-labeled analogues migrating from the light-blocking region of the substrate into the transparent region of void volume. The distance of migration increases with the thickness of the device, and leads to undesirable increases in response time. Preferably, the thickness of the device as measured from exterior surface to exterior surface is less than about 1000 microns. More preferably, this thickness is less than about 750 microns. Still more preferably, this thickness is less than about 500 microns.

Preferably, the widths of devices in accord with the present invention do not exceed about 10 millimeters. More preferably, widths are less than about 5 millimeters. Preferably, the lengths of devices in accord with the present invention do not exceed about 30 millimeters. More preferably, lengths are less than about 10 millimeters.

The shape of a device intended for in vivo applications is ultimately governed by the manner of implantation of the device into the subcutaneous tissue of a patient. Preferably, implantation is achieved with a syringe, in order to minimize the invasiveness of the procedure. Thus, it is preferred that the edges of the device be rounded to reduce friction points with the interior surface of the syringe needle. Suitable shapes for the device, as viewed along an axis perpendicular to the exterior surface of the first membrane, include but are not limited to rectangular, square, circular, elliptical, obround, and the like. Explantation of the device can be achieved by making an incision in the skin overlying the site of implant, and by removing the device using, for example, forceps, tweezers, or other instruments known in the art.

Specific Embodiments

In a first preferred embodiment, the analyte is glucose, the substrate is one or a plurality of dyed porous beads comprised of dextran having glucose binding sites within the pores such as are sold under the tradename of SEPHADEX (Amersham Pharmacia), and the analogue is fluorescently-labeled Concanavalin-A. At a low concentration of glucose, fluorescently-labeled Concanavalin-A (Con-A*) binds to glucose binding sites inside the pores of the dyed SEPHADEX beads. As the concentration of glucose increases, the glucose displaces Con-A* from the glucose binding sites in the beads. Con-A* migrates outside the beads, is excited by the light from which it had previously been shielded, and fluoresces. The amount of Con-A* displaced from the beads and, correspondingly, the amount of fluorescence generated, are dependent on the concentration of glucose. The competitive binding reactions between the Con-A*/glucose site and the Con-A*/glucose analyte can be expressed as in equations (I) and (II), where "Glucose Site" refers to a binding site:

Con-A*+Glucose Site⇌Con-A*/Glucose Site        (I)

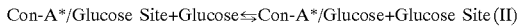
Con-A*/Glucose Site+Glucose⇌Con-A*/Glucose+Glucose Site (II)

In a second preferred embodiment, the analyte is glucose, the substrate is one or a plurality of dyed SEPHADEX beads modified to incorporate Concanavalin-A binding sites within the pores, and the analogue is fluorescently-labeled dextran. At a low concentration of glucose, fluorescently-labeled dextran (Dex*) binds to the Concanavalin-A binding sites inside the pores of the dyed SEPHADEX beads. As the concentration of glucose increases, the glucose displaces the Dex* from the Concanavalin-A binding sites in the beads. Dex* migrates outside the beads, is excited by the light from which it had previously been shielded, and fluoresces. The amount of Dex* displaced from the beads and, correspondingly, the amount of fluorescence generated, are dependent on the concentration of glucose present. The competitive binding reactions between the Dex* and the glucose analyte can be expressed as in equations (III) and (IV), where "Con-A Site" refers to a binding site:

  (III)

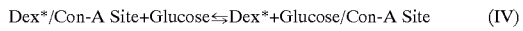  (IV)

Figure 2:
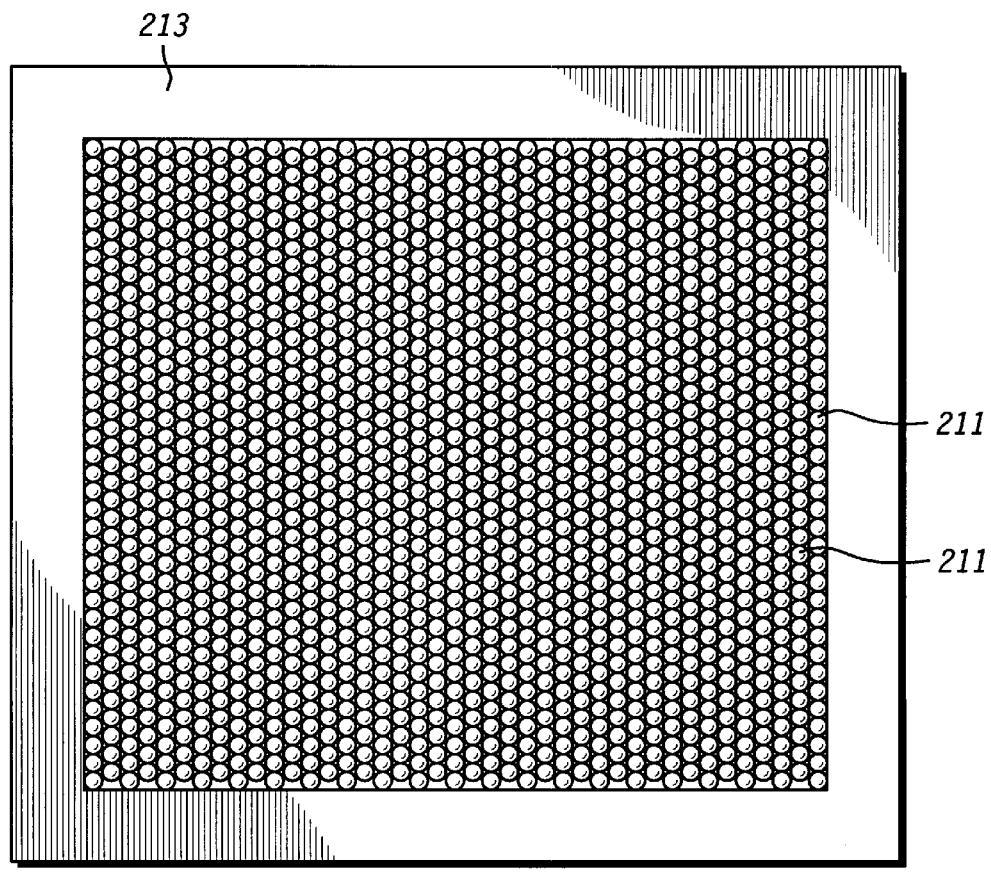
FIG. 2 is a top view of the device shown in FIG. 1.

FIGS. 1 and 2 show a device 201 embodying preferred features of the present invention, and comprising a support 205, a substrate 211, a spacer 213, a first membrane 215, and a second membrane 225. The support 205 has an interior surface 207 and an exterior surface 209. A plurality of substrates 211 is immobilized on the interior surface 207 of support 205. The spacer 213 encompasses the plurality of substrates 211. A first membrane 215 having an interior surface 217 and an exterior surface 219, and a second membrane 225 having an interior surface 227 and an exterior surface 229, are permeable to analyte 203 (not shown) but impermeable to the labeled analogue 231 (not shown). A chamber 220 enclosing substrate 211 is defined by the interior surface 207, the spacer 213, and the interior surface 217. The spacer 213 exceeds the substrate 211 in elevation such that a void volume 221 exists between the interior surface 217 and the substrate 211.

Preferably, the device 201 has at least one surface that is permeable to the analyte and, more preferably, has at least two such surfaces. In the embodiment shown in FIGS. 1 and 2, the analyte-permeable surfaces can be provided by one or both of membranes 215 and 225. The impermeability of the two membranes 215 and 225 to the labeled analogue 231 ensures that the total amount of labeled analogue in the device remains constant. In the event that one or more of substrates 211 become detached from support 205, (e.g., if immobilization is achieved with an adhesive), it is preferred that membranes 215 and 225 be likewise impermeable to substrate 211. Thus, the amounts of substrate 211 and labeled analogue 231 in device 201 remain constant, whereas the amount of analyte 203 varies.

Furthermore, the device 201 has at least one surface that is substantially transparent to the excitation and emission wavelengths of the fluorescently-labeled analogue. For example, in the embodiment shown in FIGS. 1 and 2, the transparent surface can be provided by first membrane 215.

In contrast to the difficulties encountered in reproducibly charging hollow fiber sensors with bioreagents (e.g., SEPHADEX beads), substrate 211 can be introduced into devices of the present invention with facility and with good reproducibility. For example, a precisely measured amount of a freeze dried mixture of dyed SEPHADEX beads and fluorescently-labeled analogue can be applied with a spatula to a PSA overlying interior surface 207.

In applications of the device 201, it is preferred that analyte 203 be able to enter the device from more than one face. In the embodiment shown in FIGS. 1 and 2, analyte-permeable surfaces can be provided by one or both of membranes 215 and 225. However, if support 205 is comprised of a material that is otherwise impermeable to analyte 203, analyte entering the device through second membrane 225 would be prevented from accessing the chamber 220. Thus, it is preferred that support 205 be permeable to analyte, or that it include one or more perforations 223 such as may be introduced by piercing support 205 with a needle or laser ablation to enable passage therethrough of analyte.

As shown in FIG. 1, immobilization of substrate 211 on support 205 provides a region of void volume 221 in chamber 220 in which the density of substrate 211 is preferably low. More preferably, the concentration of substrate 211 in void volume 221 is negligible, resulting in a region that is substantially free of the light absorbing dye attached to the bead. In embodiments in which SEPHADEX beads are attached to a PSA overlying support 205, it is conceivable that a bead may occasionally become detached from the interior surface 207 and migrate into void volume 221. Nonetheless, the density of substrate 211 in void volume 221 will be substantially less than the corresponding density at the surface 207.

In contrast to the difficulties encountered during the implantation and explantation of hollow fiber sensors in the subcutaneous tissue of a patient, devices in accord with the present invention will be substantially less prone to damage. Spacer 213 provides the device 201 with rigidity, and serves to preserve the structural integrity of the unit during implantation and explantation.

Figure 4:
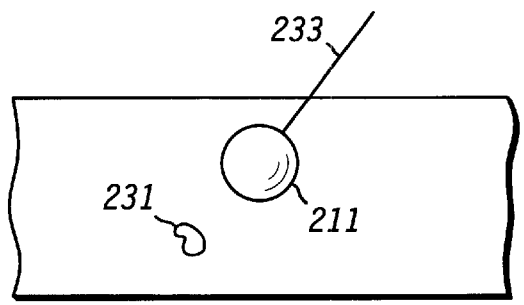
FIG. 4 is a cross-sectional side view of a hollow fiber sensor subjected to the shadowing effect.

Devices 201 in accord with the present invention provide fluorescence signals with substantially better signal-to-noise ratios than are observed for hollow fiber sensors. While it is not the Applicants' desire to be bound by a particular theory, it is believed that the explanation for the improved signal-to-noise ratios may involve the larger cross-section of the device 201 as compared to the narrow cross-section of the hollow fiber sensors, as well as the minimization or avoidance of the undesirable shadowing effect that occurs in hollow fiber sensors and which would potentially occur in device 201 if substrate 211 were not immobilized on support 205. The shadowing effect is illustrated in FIG. 4, in which the substrate 211 (e.g., a SEPHADEX bead) is interposed between incoming excitation wavelength 233 and the fluorescently-labeled analogue 231. As a consequence of this interposition, labeled analogue 231 fails to fluoresce and the overall fluorescence signal is reduced. By immobilizing the substrate 211 in accord with the present invention, void volume 221 is substantially free of materials the presence of which would prevent incoming excitation wavelengths from interacting with labeled analogue 231.

In monitoring an analyte in accord with the present invention, the excitation and emission of fluorescence is achieved with an extracutaneous optical unit positioned in proximity to the site of implantation. The optical unit includes a laser (or other light emitting device such as an LED) for emitting light having the requisite excitation wavelength to initiate fluorescence from the labeled analogue, and a photodetector for detecting fluorescence emitted by the labeled analogue. The fluorescence detected by the photodetector is correlated with a concentration of glucose in the blood. In preferred embodiments, the device is implanted in the wrist or upper arm of a patient, thereby enabling the optical unit to be inconspicuously contained in a wristwatch-like or pager-like housing. Preferred optical units are described in copending application, entitled "System using a portable detection device for detection of an analyte through body tissue", Ser. No. 09/832,521, filed Apr. 11, 2001.

The manner in which a device embodying features of the present invention is made, and the process by which such a device is used for monitoring an analyte, will be abundantly clear to one of ordinary skill in the art based upon joint consideration of both the preceding description, and the following representative procedures.

Excitation Sources and Detectors

Many excitation sources which produce light at the absorption wavelengths of the fluorescent label are available. Some possibilities include lasers and LEDs. Lasers are preferred when the device is implanted in a human because of their high power, narrow spectral linewidth, and fast response time. A laser emitting between 630 and 1200 nm, inclusive, is preferred since skin is substantially transparent within these wavelengths.

Many detection systems may be used, including but not limited to photodiodes, avalanche diodes, CCDs, and photomultipliers.

Calibration of the emission signal of the fluorescent label may be effected by ratiometrically relating it to that of the reference. Thus, the fluorescent label and reference may be irradiated with light of a specific wavelength, more than one specific wavelength, or a range of wavelengths, which may or may not be the wavelength of maximum absorption. The fluorescence emission may be measured at specific wavelengths, which may or may not be the wavelength of maximum emission intensity, or a range of wavelengths in conjunction with specific light filtering devices. By this procedure, the fluorescence emission of the fluorescent label may be discerned from that of the reference. Expressing the emission of the fluorescent label as a fraction of the emission of the reference yields a signal ratio that is sensitive to the analyte of interest and less sensitive to the effects of misalignment of the implant and detector than a single fluorescent label sensor composition. In this manner, the amount of analyte can be quantitated.

Method of Detecting Analyte

A method for monitoring an analyte embodying features of the present invention includes (a) implanting into a subcutaneous region of a patient a device in accordance with the present invention; (b) illuminating an extracorporeal region of the patient with a light having a wavelength which corresponds to the excitation wavelength of a fluorescently-labeled analogue contained in the device; (c) detecting a fluorescence signal corresponding to the emission wavelength of the fluorescently-labeled analogue using an extracorporeal photodetector; and (d) correlating the fluorescence signal with a concentration of the analyte.

EXAMPLES

The reagents and materials used in the following representative procedures were obtained from the following sources:

| MATERIAL | SUPPLIER |
| --- | --- |
| Concanavalin A | Sigma, St. Louis, MO, USA |
| SEPHADEX G200 (superfine) | Amersham Pharmacia, Piscataway, NJ, USA |
| Divinyl sulphone (DVS) | Sigma |
| Alkali Blue 6B | Sigma |
| Glycine | Sigma |
| Sodium carbonate | Sigma |
| Sodium hydrogen carbonate | Sigma |
| Phosphate buffered solution (prepared vials) | Sigma |
| Dimethyl sulfoxide | Aldrich, St. Louis, MO, USA |
| ALEXA633-Concanavalin A | Molecular Probes, Eugene, OR, USA |
| Superglue, Loctite454 | Loctite, Rocky Hill, CT |
| VHB ™ double coated acrylic foam Tape and adhesive transfer tape | 3M, Minneapolis, MN, USA |
| SnakeSkin ™ cellulose membrane | Pierce, Rockford, IL, USA |

Example 1

Labeled Analogue is ConA with a SEPHADEX Substrate

Dyeing of SEPHADEX Beads

For the dyeing procedure the DVS-method previously described by Porath et al. (Porath, J.; Laas, T.; Janson, J.-C. J. Chromatography, 1975, 103, 49–62) was applied. SEPHADEX G200 beads were pre-swollen in 20 ml distilled water overnight. The beads were washed over a sieve with several volumes of distilled water. The bead suspension (12 ml) was then mixed with 12 ml of a 1 M sodium carbonate buffer solution ($Na_2CO_3$, pH 11.4) in a beaker. The suspension was intensively stirred on a magnetic stirrer for the duration of the procedure. DVS (800 µl) was added to the suspension and the reaction allowed to proceed for 1 hour. The beads were washed over a sieve with copious amounts of distilled water to remove non-bound DVS, and subsequently equilibrated with 0.5 M sodium hydrogen carbonate buffer ($NaHCO_3$, pH 11.4). Alkali Blue 6B (30 mg) was dissolved in DMSO (1 ml). The resultant solution was then slowly added to the stirred suspension and the reaction was allowed to proceed overnight. Then glycine (1 g) was introduced into the mixture to neutralize remaining active DVS groups. After 1 hour, the beads were transferred into a 15 ml plastic vial and centrifuged in order to remove non-bound dye molecules. The supernatant was discarded. The beads were re-suspended in DMSO, shaken, and centrifuged again. This procedure was repeated several times until the supernatant was color-free. The bead suspension was then equilibrated with PBS and stored in the refrigerator at 4° C.

Preparation of ALEXA633-Con-A/Alkali Blue 6B-SEPHADEX

A small volume of a wet suspension of Alkali Blue 6B-SEPHADEX (0.7 ml) was pipetted into a 1 ml pipette tip the outlet of which was blocked with a small piece of filter paper to prevent the beads from passing through. After the bead suspension settled, 1 ml of 10 mg ALEXA633TM Con A was passed through the column which was then rinsed with one column volume of PBS buffer. The suspension was then transferred to a 1.5 ml tube. The tube was frozen at −20° C. for 60 min and subsequently freeze-dried. The blue powder was stored at 4° C. until further use.

Manufacturing of Sensor Package

A rectangular piece of pressure sensitive adhesive tape (VHB, 3M, F-9473PC), hereinafter PSA, with dimensions of 3×2 cm was cut with scissors. Two narrow pieces of the PSA (3×0.5 cm) were cut and put onto the sticky side of the base PSA leaving an adhesive-coated channel in between. They act as spacers leaving a narrow gap, or free space between the bead-coated surface and the membrane. The channel was randomly perforated using a needle with a sharp tip (gauge #32). Then the tip of a spatula containing freeze-dried powder of ALEXA633-Con A and Alkali Blue-SEPHADEX was carefully put on the sticky surface of the PSA. The powder was evenly spread onto the PSA with the flat end of a spatula exerting weak pressure until the narrow channel was entirely covered with the blue beads. Tapping the PSA on the table removed non-sticking beads. The backings of the two narrow PSA pieces along the side of the coated PSA were removed with forceps. A piece of cellulose membrane (SnakeSkin™, Pierce) matching the size of the prepared bead-coated PSA was cut and adhered to the sticky tape. Gentle pressure was exerted on the membrane to ensure good bonding with the adhesive. Then the package was flipped on its backside and the adhesive-bearing support layer was peeled off. A piece of cellulose membrane (5×3 cm), which was slightly longer then the package, was cut. The membrane was then put on the adhesive-coated surface by centering the package leaving two free ends of the membrane on both sides of the package. Again, gentle pressure was applied to the membrane to provide good bonding. Then the package was cut along its longer axis with scissors into narrow pieces (approximate width 0.7 cm), yielding four sensor packages. To finish the manufacturing of sensor packages, a sensor was grabbed at the ends of the membrane with forceps. Superglue (Loctite 454) was carefully coated with a fine tip onto the ends where the PSA spacer is sandwiched between the two membranes. Then a small volume of buffer solution (20 µl) is injected into the gap separated by the membrane and the bead coated support using a Hamilton pipette. The sides were then carefully and quickly sealed with adhesive too. The package was submersed into buffer solution where the adhesive immediately polymerized. This formed a tight seal around the edges of the sensor package. Air bubbles that were still trapped inside the sensor were removed by storing the sensor in a degassed buffer solution at 4° C.

Example 2

Labeled Analogue is Glucose-Modified ALEXA633-Albumin with a SEPHAROSE®-Con Substrate Dyeing of SEPHAROSE® Beads:

For dyeing SEPHAROSE® 4B (Sigma, St. Louis, Mo., USA) with Alkali Blue 6B, the same procedure as above (e.g., using divinyl sulfone) was employed.

Conjugation of Alkali Blue 6B-SEPHAROSE® with Concanavalin A Using Periodate-oxidation A suspension of 4 ml Allcali Blue-SEPHAROSE® was washed in distilled water. Then 1 ml of 50 mg $NaIO_4$ dissolved in distilled water was slowly added to the suspension. The suspension was gently shaken and incubated for 60 minutes. Then, the oxidation reaction was stopped by adding 2 ml of 2 M ethylene glycol (Sigma) and incubated for 30 min at room temperature. The activated SEPHAROSE® suspension was washed several times with 10 ml of 0.01 M sodium carbonate buffer (pH 9.2). 100 mg of Concanavalin A dissolved in 3 ml of sodium carbonate buffer containing 1 mM of calcium chloride and 50 mM of Methyl-mannose (Sigma), was added to the suspension and stirred for 12 hours at room temperature (22° C.). The Concanavalin A-conjugated Alkali Blue-SEPHAROSE® was washed with phosphate buffered saline (pH 7.2) containing 1 mM of calcium chloride until the supernatant was free of Concanavalin A measured at 280 nm. The suspension was stored at 4° C.

Conjugation of Albumin with Glucose and ALEXA633:

ALEXA633 was covalently linked to albumin using the ALEXA633 protein conjugation kit supplied by Molecular Probes. 5 mg of glucosepyranosylphenyl isothiocyanate (glucose-PITC, Sigma) was pre-dissolved in 30 µl of dimethylsulfoxide and 500 µl of sodium carbonate was added to this solution. 20 mg of ALEXA633-albumin was dialyzed against 50 mM of sodium carbonate buffer at a pH of 9.4, and mixed with the solution of glucose-PITC. The mixture was gently shaken and the reaction was allowed to proceed at 4° C. for 15 hours. Glucose-modified-ALEXA633-albumin conjugate was separated from non-reacted glucose-PITC by size exclusion chromatography using SEPHADEX G50.

Preparation of ALEXA633-Glucose-Albumin/Alkali Blue 6B-ConA-SEPHAROSE®:

A small volume of wet suspension of Alkali Blue 6B-Con A-SEPHAROSE® (0.7 ml) was pipetted into a 1 ml pipette tip the outlet of which was blocked with a small piece of filter paper to prevent the beads from passing through. After the bead suspension settled down, 1 ml of 10 mg ALEXA633-glucose-albumin was passed through the column, which then was rinsed with one column volume of PBS buffer. The suspension was then transferred to a 1.5 mL tube. The tube was frozen at −20° C for 60 min and subsequently freeze-dried. The blue powder was stored at 4° C. until further use.

Manufacturing of Sensor Package:

The same procedure was used as described for the Con A/SEPHADEX system.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A device for monitoring an analyte, comprising:
   a support having an interior surface and an exterior surface;
   a substrate connected to the interior surface of the support, wherein the substrate is opaque;
   a spacer connected to me interior surface of the support;
   a labeled analogue, which binds reversibly to the substrate; and
   a first membrane having an interior surface and an exterior surface, the interior surface being connected to the spacer; wherein
      the first membrane is permeable to the analyte and impermeable to the labeled analogue, and the first membrane is substantially transparent to each of an excitation wavelength and an emission wavelength of a fluorescent label;
      a dye absorbs a majority of the excitation and emission wavelengths of the fluorescent label;
      the interior surface of the support, the spacer, and the interior surface of the first membrane define a chamber which encloses the substrate and the labeled analogue, the chamber further comprises a reference; and
      the spacer exceeds the substrate in elevation such that a void volume exists between the interior surface of the first membrane and the substrate.

2. The device of claim 1, wherein the support comprises an adhesive whereby the substrate is immobilized.

3. The device of claim 1, wherein the labeled analogue further comprises a glucose-containing moiety.

4. The device of claim 3, wherein the substrate is intrinsically opaque, or comprises a dye selected from the group consisting of Alkali Blue 6B, Azure A, Evans Blue and Celestine Blue.

5. The device of claim 1, wherein the spacer is comprised of a biocompatible material selected from the group consisting of titanium, stainless steel, acrylate derivatives, silicones, fluorosiloxanes, PTFE, polyimide, polyamide, halogenated hydrocarbon polymers, silica, and urethanes.

6. The device of claim 1, wherein the support comprises an adhesive selected from the group consisting of methyl methacrylate, acrylate derivatives, urethanes, silicones, fluorosiloxane, epoxies, cyanoacrylates and cyanoacrylate esters, whereby the substrate is immobilized.

7. The device of claim 1, wherein the support comprises a hydrogel whereby the substrate is immobilized.

8. The device of claim 1, wherein the substrate is chemically bonded to the interior surface of the support.

9. The device of claim 1, wherein the analyte is glucose.

10. The device of claim 1, wherein the spacer encompasses the substrate.

11. The device of claim 1, wherein the substrate comprises a plurality of pores sufficiently large to permit ingress and egress of the labeled analogue.

12. The device of claim 11, wherein the substrate is comprised of a dextran bead, which bead comprises a plurality of glucose binding sites within the pores.

13. The device of claim 12, wherein the support comprises an adhesive whereby the substrate is immobilized.

14. The device of claim 12, wherein the labeled analogue comprises Concanavalin A.

15. The device of claim 14, wherein the substrate comprises a dye selected from the group consisting of Alkali Blue 6B, Azure A, Evans Blue, and Celestine blue.

16. The device of claim 1, wherein the excitation wavelength of the fluorescent label is substantially the same as an excitation wavelength of the reference, and wherein an emission wavelength of the reference is substantially longer than the emission wavelength of the fluorescent label.

17. The device of claim 16, wherein the reference is selected from the group consisting of quantum dots, tracer dyes, and phycobiliproteins.

18. The method claim 1, further comprising:
   detecting the amount of emission from the reference; and
   quantitating the amount of analyte based on the amount of emission from the reference.

19. The device of claim 1, wherein the labeled analogue is selected from the group consisting of a labeled antibody, a labeled lectin, a labeled enzyme, a labeled polymer, and combinations thereof.

20. The device of claim 1, wherein the support is perforated or permeable to the analyte.

21. The device of claim 20, further comprising a second membrane having an interior surface and an exterior surface, wherein the second membrane is permeable to the analyte and impermeable to the labeled analogue, and wherein the interior surface of the second membrane is connected to the exterior surface of the support.

22. The device of claim 21, wherein the first and second membranes are comprised of a biocompatible material selected from the group consisting of cellulose acetate, polysulfones, polycarbonates, poly(vinyl chlorides), polyamides, ethylene vinyl acetate copolymers, poly(vinylidene) fluoride, poly(urethanes), poly(benzimidazoles), cellulose esters, cellulose triacetate, cellulose, cellulose nitrate, regenerated cellulose, cross-linked poly(vinylpyrrolidone); crosslinked polyacrylamide, crosslinked poly (hydroxy ethyl methacrylate), silicones, fluorosiloxanes, PTFE, and combinations thereof, and wherein the biocompatible material is optionally coated with a biocompatibility-promoting substance selected from the group consisting of polyethylene glycol, basic fibroblast growth factor, and angiogenic substances.

23. The device of claim 21, wherein the exterior surface of the first membrane and the exterior surface of the second membrane are separated by less than about 1000 microns.

24. The device of claim 21, wherein the exterior surface of the first membrane and the exterior surface of the second membrane are separated by less than about 750 microns.

25. The device of claim 21, wherein the exterior surface of the first membrane and the exterior surface of the second membrane are separated by less than about 500 microns.

26. The device of claim 1, being substantially flat and square in shape as viewed along an axis perpendicular to the exterior surface of the first membrane.

27. The device of claim 26, wherein the square has a diameter between about 1 millimeter and about 10 millimeters.

28. The device of claim 1, being substantially flat and rectangular in shape as viewed along an axis perpendicular to the exterior surface of the first membrane.

29. The device of claim 28, wherein the rectangle has a width less than about 10 millimeters, and a length less than about 30 millimeters.

30. The device of claim 1, being substantially flat and elliptical in shape as viewed along an axis perpendicular to the exterior surface of the first membrane.

31. The device of claim 30, wherein the ellipse has a minor axis less than about 10 millimeters, and a major axis less than about 30 millimeters.

32. The device of claim 1, being substantially flat and circular in shape as viewed along an axis perpendicular to the exterior surface of the first membrane.

33. The device of claim 32, wherein the circle has a diameter less than about 10 millimeters.

34. The device of claim 1, wherein a ratio of the void volume to a volume occupied by the substrate is between about 1 and about 5.

35. The device of claim 34, wherein the ratio is less than about 3.

36. The device of claim 34, wherein the ratio is about 1.

37. The device of claim 1, wherein a weight ratio of the labeled analogue to the substrate is between about 0.1 to about 10.

38. The device of claim 1, wherein the dye is attached to the substrate by a divinyl sulfone linker.

39. A method for monitoring an analyte, comprising:
   (a) implanting into a subcutaneous region of a patient a device comprising:
      a support having an interior surface and an exterior surface;
      a substrate connected to the interior surface of the support;
      a labeled analogue, which binds reversibly to the substrate;
      a spacer connected to the interior surface of the support and encompassing the substrate; and
      a first membrane having an interior surface and an exterior surface, the interior surface being connected to the spacer; wherein
         the first membrane is penneable to the analyte and impermeable to the labeled analogue;
         the interior surface of the support, the spacer, and the interior surface of the first membrane define a chamber which encloses the substrate and the labeled analogue, the chamber further comprises a reference; and
         the spacer exceeds the substrate in elevation such that a void volume exists between the interior surface of the first membrane and the substrate;
   (b) illuminating an extracutaneous region of the patient with a light having a wavelength which corresponds to an excitation wavelength of a fluorescent label;
   (c) detecting a fluorescence signal corresponding to the emission wavelength of the fluorescent label with an extracutaneous photodetector; and
   (d) correlating the fluorescence signal with a concentration of the analyte.

40. The method of claim 39, wherein the analyte is glucose.

41. The method of claim 39, wherein the implanting of the device is such that the exterior surface of the first membrane is positioned parallel to an external dermal layer of the patient.

42. A device for monitoring glucose, comprising:
   a perforated support comprising an adhesive surface,
   a dextran bead comprising Alkali Blue 6B dye and at least one Concanavalin-A binding site, wherein the bead is connected to the adhesive surface of the support;

a spacer connected to the support; a labeled analogue comprising dextran labeled with a succinimidyl ester dye;

a first membrane comprising cellulose acetate, the first membrane having an interior surface and an exterior surface, wherein the interior surface is connected to the spacer; and a second membrane having an interior surface and an exterior surface, wherein the interior surface is connected to the support; wherein the First and second membranes are permeable to the glucose and impermeable to the labeled analogue;

the adhesive surface, the spacer, and the interior surface of the first membrane define a chamber which encloses the bead and the labeled analogue; and the spacer exceeds the bead in elevation such that a void volume exists between the interior surface of the first membrane and the bead.

* * * * *

UNITED STATES PATENT AND TRADEMARK OFFICE
CERTIFICATE OF CORRECTION

PATENT NO. : 6,454,710 B1  
DATED : September 24, 2002  
INVENTOR(S) : Ballerstadt et al.

It is certified that error appears in the above-identified patent and that said Letters Patent is hereby corrected as shown below:

Column 14,
Line 19, reads "me", should be -- the --.

Column 16,
Line 40, reads "penneable", should be -- permeable --.

Signed and Sealed this

Thirty-first Day of August, 2004

JON W. DUDAS
*Director of the United States Patent and Trademark Office*